United States Patent [19]

Yamaguchi et al.

[11] Patent Number: 4,729,848

[45] Date of Patent: * Mar. 8, 1988

[54] METAL SALTS OF ALKYL CATECHOL DITHIOPHOSPHORIC ACIDS AND OIL COMPOSITIONS CONTAINING THE SALTS

[75] Inventors: Elaine S. Yamaguchi, El Cerrito; Thomas V. Liston, San Rafael, both of Calif.

[73] Assignee: Chevron Research Company, San Francisco, Calif.

[ * ] Notice: The portion of the term of this patent subsequent to May 26, 2004 has been disclaimed.

[21] Appl. No.: 904,992

[22] Filed: Sep. 8, 1986

Related U.S. Application Data

[63] Continuation of Ser. No. 537,628, Sep. 30, 1983, abandoned.

[51] Int. Cl.$^4$ ............... C07F 3/06; C10M 105/08; C10M 107/22
[52] U.S. Cl. ................ 252/32.7 E; 556/25; 558/86
[58] Field of Search ............ 556/25; 252/32.7 E; 558/86

[56] References Cited

U.S. PATENT DOCUMENTS

| | | | |
|---|---|---|---|
| 2,410,650 | 11/1946 | Giammaria | 252/33.6 |
| 2,480,673 | 8/1949 | Reiff et al. | 252/32.7 |
| 2,506,570 | 5/1950 | Andress et al. | 252/32.7 |
| 2,540,084 | 2/1951 | Asseff | 260/429 |
| 3,327,024 | 6/1967 | DeYoung et al. | 260/925 |
| 3,428,662 | 2/1969 | Millendorf et al. | 260/429.9 |
| 3,489,682 | 1/1970 | Le Suer | 252/32.7 |
| 3,515,712 | 6/1970 | Goldsmith | 260/139 |
| 3,687,848 | 8/1972 | Colclough et al. | 252/32.7 |
| 4,010,107 | 3/1977 | Rothert | 252/32.7 |
| 4,085,053 | 4/1978 | Caspari | 252/32.7 E |
| 4,113,634 | 9/1978 | Sabol et al. | 252/32.7 E |
| 4,443,360 | 4/1984 | Yamaguchi et al. | 252/46.7 |

OTHER PUBLICATIONS

Smolenski et al, SAE Technical Paper Series, 831760 (1983) pp. 115–128.

*Primary Examiner*—Helen M. S. Sneed
*Attorney, Agent, or Firm*—S. R. LaPaglia; R. C. Gaffney; J. J. DeYoung

[57] ABSTRACT

Metal salts of alkyl catechol esters of dithiophosphoric acid suitable as additives in oil compositions are disclosed. Oil compositions containing the salts of such esters show improved extreme pressure/anti-wear and anti-oxidant properties.

9 Claims, No Drawings

METAL SALTS OF ALKYL CATECHOL DITHIOPHOSPHORIC ACIDS AND OIL COMPOSITIONS CONTAINING THE SALTS

This is a continuation of application Ser. No. 537,628, filed Sept. 30, 1983 now abandoned.

BACKGROUND OF THE INVENTION

1. Field of the Invention

The invention relates to novel alkyl catechol esters of dithiophosphoric acids, their salts, and to oil compositions containing such salts.

2. Description of the Prior Art

It is known to add compounds to oils in order to improve the load-bearing properties, e.g., extreme pressure and/or anti-wear properties thereof.

One class of such compounds are the metal salts of dihydrocarbyl dithiophosphoric acids, e.g., the zinc salts thereof, which are well known as load-bearing additives for lubricating oils. Such salts may be represented by the formula:

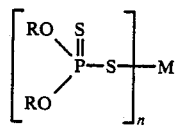

wherein:

R is the same or different optionally substituted hydrocarbyl group;

M is a metal; and n corresponds to the valence of the metal M.

Many types of additives have been proposed, e.g., those in which the optionally substituted hydrocarbyl groups represented by R are the same or different alkyl, cycloalkyl, aryl groups, e.g., see U.S. Pat. Nos. 2,410,642, 2,540,084, 2,506,570, and 4,212,751; U.K. Patent Nos. 723,133 and 852,365; as well as groups derived from alkoxylated alcohols and monoester alcohols, e.g., see U.K. Patent. No. 2,070,054 and U.S. Pat. Nos. 3,102,096 and 4,288,335.

The metal dialkyl dithiophosphates are effective anti-wear agents in oils formulated for gasoline engines, however, they do not function well in diesel engines due to their thermal instability.

Metal diaryl dithiophosphates such as metal phenyl or alkylphenyl dithiophospates are effective in achieving good diesel performance as evidenced by relatively lower piston deposits, however, they are generally not as effective anti-wear agents as the dialkyl dithiophospates in gasoline engines.

It has now been found that oil compositions containing the metal alkyl catechol esters of dithiophosphoric acid of this invention show excellent extreme pressure and anti-wear properties as evidenced by valve train wear performance in gasoline engines while achieving good diesel engine performance.

SUMMARY OF THE INVENTION

This invention is concerned with metal salts of dithiophosphoric acid esters of the general formula:

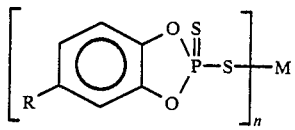

wherein R is alkyl containing 10 to 18 carbon atoms or mixtures thereof, M is an alkali or alkaline earth metal or transition metal, and n corresponds to the valence of the metal M.

The invention further provides oil compositions comprising a major amount of an oil of lubricating viscosity and a minor amount sufficient to inhibit oxidation and wear of the metal salts of the Formula I or mixtures thereof.

DETAILED DESCRIPTION

The metal salts of the Formula I of this invention may be prepared by the neutralization of the alkyl catechol esters of dithiophosphoric acid of the Formula II:

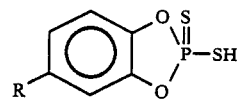

or mixtures thereof, wherein R is defined above, with a basic metal compound such as an alkali or alkaline earth metal or transition metal hydroxide, carbonate or oxide and preferably the metal is selected from the Groups IIB, IIIB, IVB, VIB or VIII of the Periodic System of Elements and, in particular, zinc.

The reaction may be carried out at a temperature of between about 25° C. and 180° C. with an amount of basic metal compound between the amount stoichiometrically necessary to neutralize the dithiophosphoric acid and twice said stoichiometric amount, and preferably between 1.1 and 1.5 times the stoichiometric amount.

The metal salt so formed may be converted to a different metal salt by double decomposition thereof with a metal salt such as a chloride or sulphate. For example, the sodium salt formed in neutralization may be converted to the zinc salt by reaction thereof with zinc sulphate. The reaction is preferably carried out in the presence of a solvent, e.g., benzene or toluene and under nitrogen. The salt may be isolated from the reaction product mixture by conventional techniques such as by extraction.

The alkyl catechol esters of dithiophosphoric acid of the Formula II:

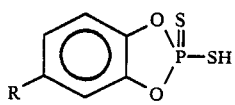

or mixtures thereof, wherein R is defined above, can be prepared by the action of phosphorus pentasulfide on an alkyl catechol or mixture of alkyl catechols of the Formula III:

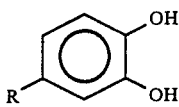

wherein R is defined above, with an amount of $P_2S_5$ corresponding to the stoichiometric quantity of $P_2S_5$. This operation may be carried out at a temperature of between about 50° C. and 200° C. and preferably between 70° C. and 150° C.

The general methods for preparing the dithiophosphoric acid esters and their corresponding metal salts are described in U.S. Pat. Nos. 3,089,850, 3,102,096, 3,293,181, and 3,489,682.

The alkyl catechols or mixtures thereof which may be used to prepare the metal salts of the Formula I have the Formula III:

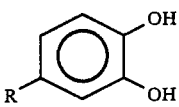

wherein R is alkyl containing 10 to 18 carbon atoms and preferably from 15 to 18 carbon atoms. Also, up to 25% by weight and preferably 15% by weight of the alkyl catechols may have the R group in a position adjacent or ortho to one of the hydroxy groups and have the Formula IV:

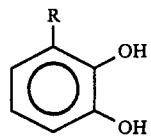

wherein R is defined above.

Among the alkyl catechols which may be employed are decyl catechol, undecyl catechol, dodecyl catechol, tetradecyl catechol, pentadecyl catechol, hexadecyl catechol, octadecyl catechol, and the like. Also, a mixture of alkyl catechols may be employed and preferably a mixture of $C_{15}$–$C_{18}$ alkyl catechols may be used.

The alkyl catechols of the Formula III may be prepared by reacting a branched- or straight-chained α-olefin containing 10 to 18 carbon atoms with pyrocatechol in the presence of a sulfonic acid catalyst, at a temperature of from about 60° C. to 200° C., and preferably 125° C. to 180° C. in an essentially inert solvent at atmospheric pressure. Molar ratios of reactants may be used and preferably a 10% by weight molar excess of α-olefin over catechol is used. Examples of the solvents include benzene, toluene, chlorobenzene, and 250. Thinner which is a mixture of aromatics, paraffins and naphthenes.

Examples of metal compounds which may be reacted with the dithiophosphoric acid include lithium oxide, lithium hydroxide, lithium carbonate, lithium pentylate, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, molybdenum oxide, and molybdenum oxysulfide.

The salts may be added to any oil, e.g., gasoline, middle distillate fuels, industrial oils, greases, etc., but are particularly suitable as additives to oils of lubricating viscosity, especially those for use in internal combustion engines.

Preferably, the oil basestock is a lubricating oil, fractions of a mineral oil such as petroleum, either naphthenic, paraffinic or as mixed naphthenic/paraffinic base, unrefined, acid-refined, hydrotreated or solvent refined as required for the particular lubricating need. In addition, synthetic oils such as ester lubricating oils and polyalphaolefins, as well as mixtures thereof with mineral oil meeting the viscosity requirements for a particular applicaton either with or without viscosity index improvers may also be used as basestock provided the above compound is soluble therein. The lubricating oil basestock preferably will have a viscosity in the range from about 5 to about 220 centistokes at 100° F. Suitable mineral oils include low, medium, high and very high viscosity index lubricating oils.

The amount of additive present in the composition may vary between wide limits but is suitably from 0.05 to 10.0% by weight with amounts of from 0.1 to 2.0% by weight being usual, based on the weight of the composition.

The lubricating compositions according to the invention may contain other components. Examples of such components include viscosity-index improvers including conjugated diolefin block copolymers and low molecular weight methacrylate polymers, dispersants (of the ash and/or ashless type), pour point depressants such as acrylate and methacrylate polymers, anti-oxidants, metal passivators and anti-corrosion agents. If desired, in addition to the present load-bearing additives, the lubricating composition may include other compounds having a load-bearing action.

Additive concentrates are also included within the scope of this invention. They usually include from about 90 to 10 weight percent of an oil, preferably an oil of lubricating viscosity, and are normally formulated to have about 10 times the additive concentration that would be used in the finished oil composition. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions.

The following examples are provided to illustrate the invention. It is understood that they are provided for the sake of illustration only and not as a limitation on the scope of the invention.

EXAMPLES

EXAMPLE 1

To a 3-liter flask, equipped with stirrer, Dean Stark trap, condenser, and nitrogen inlet and outlet was charged 759 gms. of a $C_{15}$-$C_{18}$ α-olefin, 330 gms. of pyrocatechol, 165 gms. of a sulfonic acid cation exchange resin (polystyrene cross-linked with divinylbenzene) catalyst (Amberlyst 15 supplied by Rohm and Haas Co.) and 240 ml. toluene. The reaction mixture was heated to 150° C. to 160° C. for about 7 hours with stirring under a nitrogen atmosphere. The reaction mixture was stripped by heating to 160° C. under vacuum (0.4 mm Hg). The product was filtered hot over super cell (SCC) to afford 908.5 gms. of $C_{15}$-$C_{18}$ alkyl substituted pyrocatechol. The product had a hydroxyl number of 259. In a similar manner, by substituting an equivalent amount of each of a $C_{12}$ α-olefin, a $C_{14}$ α-olefin and a $C_{18}$ α-olefin in the above procedure, the corresponding alkyl catechols are prepared.

EXAMPLE 2

To a dry, nitrogen-flushed, 5-liter flask, equipped with mechanical stirrer, dropping funnel, reflux condenser, and a caustic scrubber were added 277.8 gms. $P_2S_5$ and 1500 ml. toluene. To this solution was added 791.5 gms. of the $C_{15}$-$C_{18}$ alkylated catechol from Example 1 dissolved in 1500 ml. toluene over a period of 20 minutes. The reaction mixture was then heated to reflux at 110° C. for about 4½ hours. The reaction mixture was cooled to room temperature and filtered through SCC. The reaction mixture weighed 3604 gms. and contained 98.3% of the $C_{15}$-$C_{18}$ alkylated catechol dithiophosphoric acid. Infrared and NMR analysis confirmed the structure of the product. The acid number of the product was 115. The product was about 85% para substituted and 15% ortho substituted.

In a similar manner, by substituting an equivalent amount of each of a $C_{12}$ alkyl substituted catechol, $C_{14}$ alkyl substituted catechol, and a $C_{18}$ alkyl substituted catechol for the $C_{15}$-$C_{18}$ alkyl substituted catechol in the above procedure, the corresponding alkyl substituted catechol dithiophosphoric acids are obtained.

EXAMPLE 3

To a nitrogen-flushed, 5-liter flask, equipped with a mechanical stirrer and reflux condenser were added 84.6 gms. of zinc oxide and 1500 ml. toluene. To the flask containing the zinc oxide was added 259.7 gms. of a toluene solution containing 657 gms. of the $C_{15}$-$C_{18}$ alkylated catechol dithiophosphoric acid prepared in Example 2 over a period of 20 minutes. The reaction mixture was heated to reflux (110° C.) and maintained at reflux for a period of 7 hours. The reaction mixture was filtered hot through SCC. The toluene was stripped off on a rotary evaporator at 90° C. and 0.3 mm. Hg vacuum to accord 690 gms. of the zinc salt of the $C_{15}$-$C_{18}$ alkylated dithiophosphoric acid. Neutron Activation analysis indicated:

% Zn=7.73; % P=5.63; and % S=9.75.

In a similar manner, by substituting an equivalent amount of each of a $C_{12}$ alkyl substituted catechol dithiophosphoric acid, a $C_{14}$ alkyl substituted catechol dithiophosphoric acid, and a $C_{18}$ alkyl substituted catechol dithiophosphoric acid for the $C_{15}$-$C_{18}$ alkyl substituted catechol in the above procedure, the corresponding zinc salts are prepared.

EXAMPLE 4

Formulated oils containing the additives shown in Table I were prepared and tested in a Sequence V-D Test, Method Phase 9-L (according to candidate test for ASTM). This procedure utilizes a Ford 2.3-liter, 4-cylinder engine. The test method simulates a type of severe field test service characterized by a combination of low speed, low temperature "stop and go" city driving and moderate turnpike operation. The effectiveness of the additives in the oil is measured in terms of the protection provided against valve train wear.

The comparisons were made in a formulated base oil CIT-CON 100N/CIT-CON 200N at 55%/45% containing 30 mmoles/kg of calcium sulfonate, 20 mmoles/kg of a calcium phenate, 8.5% of a polymethacrylate V.I. improver, and 3.5% of a 50% concentrate of polyisobutenyl succinimide. Sufficient zinc dithiophosphates were added to give 0.05% (8.1 mmoles/kg) phosphorous to the oil.

TABLE I

| | | Sequence V-D Test | | | |
| | | Cam Lobe Wear, mils | | Follower Weight Loss, mg. | |
| Entry | Additive (8.1 mm/kg) | SF Spec. Max. (2.5) | SF Spec. Avg. (1.0) | Max. | Avg. |
| 1. | Compound of Example 3 - zinc salt of $C_{15}$-$C_{18}$ alkyl substituted catechol dithiophosphoric acid | 0.8 | 0.6 | 6 | 2 |
| 2. | 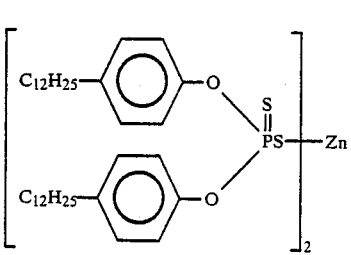 | 7.9 | 4.8 | 234 | 44 |

The test data indicate that the metal salts of alkyl catechol dithiophosphoric acid of the invention are effective anti-wear agents as compared to known metal salts of alkylphenyl dithiophosphoric acid.

EXAMPLE 5

The compositions were tested in a Caterpillar 1-G2 test in which a single-cylinder diesel engine having a 5⅛" bore by 6½" stroke is operated under the following conditions: timing, degrees BTDC, 8; brake mean effective pressure, psi 141; brake horsepower 42; Btu's per minute 5850; speed, 1800 RPM; air boost, 53" Hg absolute, air temperature in, 255° F; water temperature out, 190° F.; and sulfur in fuel, 0.4%w. At the end of each 12 hours of operation, sufficient oil is drained from the crankcase to allow addition of 1 quart of new oil. In the test on the lubricating oil compositions of this invention, the 1-G2 test is run for 60 hours. At the end of the noted time period, the engine is dismantled and rated for cleanliness. The Institute of Petroleum Test Number 247/69 merit rating system for engine wear and cleanliness, accepted by ASTM, API and SAE, is the rating system used to evaluate the engine. The overall cleanliness is noted as WTD, which is the summation of the above numbers. Lower values represent cleaner engines.

The base oil used in this test is CIT-CON 350N base oil containing 2.63% of a 50% concentrate in oil of an isobutenyl succinimide, 9.05 mmoles/kg calcium sulfonate, 10 mmoles/kg overbased calcium sulfonate, 10 mmoles/kg calcium polypropylene phenate and 8.25 mmoles/kg zinc dialkyl dithiophosphate.

TABLE II

| Formulation | Caterpillar 1-G2 Test | | | |
| --- | --- | --- | --- | --- |
| | Groves | Lands | Top Grove Fill % | WTD |
| Base Formulation | 69-92-4-0 | 47-9-5 | 68 | 226 |
| Base Formulation + 22 mmoles/kg zinc | 45-71-3-1 | 27-15-12 | 39 | 173 |

TABLE II-continued

| Formulation | Caterpillar 1-G2 Test | | | |
| --- | --- | --- | --- | --- |
| | Groves | Lands | Top Grove Fill % | WTD |
| salt of $C_{15}-C_{18}$ alkyl substituted catechol of Example 3 | | | | |

What is claimed is:

1. A compound of the formula:

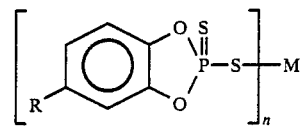

wherein R is alkyl containing 10 to 18 carbon atoms or mixtures thereof, M is an alkali or alkaline earth metal or transition metal, and n corresponds to the valence of M.

2. The compound of claim 1 wherein M is zinc.

3. The compound of claim 1 wherein R is alkyl of 15 to 18 carbon atoms or mixtures thereof.

4. The compound of claim 1 wherein R is alkyl having a range of from 15 to 18 carbon atoms, M is zinc and n is 2.

5. A lubricating oil composition comprising an oil of lubricating viscosity and from 0.05 to 10.0% by weight based on the composition of a compound according to claim 1.

6. The oil composition of claim 4 wherein M is zinc.

7. The oil composition of claim 4 wherein R is alkyl of from 15 to 18 carbon atoms or mixtures thereof.

8. The oil composition of claim 4 wherein R is alkyl having a range of from 15 to 18 carbon atoms, M is zinc and n is 2.

9. An oil concentrate comprising 10 to 90 weight percent of an oil of lubricating viscosity and from 90 to 10 weight percent of a compound according to claim 1.

* * * * *